(12) United States Patent
Roose et al.

(10) Patent No.: US 9,572,683 B2
(45) Date of Patent: Feb. 21, 2017

(54) ACETABULAR ORTHOPAEDIC SURGICAL INSTRUMENT AND METHOD OF USING SAME

(71) Applicant: DEPUY SYNTHES PRODUCTS, INC., Raynham, MA (US)

(72) Inventors: Jeffrey R. Roose, Milford, IN (US); Darron G. Peddle, Millersburg, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 799 days.

(21) Appl. No.: 13/803,780

(22) Filed: Mar. 14, 2013

(65) Prior Publication Data

US 2014/0088603 A1    Mar. 27, 2014

Related U.S. Application Data

(60) Provisional application No. 61/706,232, filed on Sep. 27, 2012.

(51) Int. Cl.
*A61F 2/46* (2006.01)
*A61B 17/17* (2006.01)

(52) U.S. Cl.
CPC ......... *A61F 2/4609* (2013.01); *A61B 17/1746* (2013.01); *A61F 2002/4687* (2013.01)

(58) Field of Classification Search
CPC ............... A61B 17/1746; A61F 2/4609; A61F 2002/4687
See application file for complete search history.

(56) References Cited

U.S. PATENT DOCUMENTS

| | | | |
|---|---|---|---|
| 7,695,476 B2 * | 4/2010 | Nevelos | A61B 17/175 606/87 |
| 2005/0148843 A1 | 7/2005 | Roose et al. | |
| 2005/0273167 A1 * | 12/2005 | Triplett | A61B 17/1757 623/17.11 |
| 2011/0015639 A1 | 1/2011 | Metzger et al. | |
| 2011/0184419 A1 | 7/2011 | Meridew et al. | |
| 2012/0041445 A1 | 2/2012 | Roose | |
| 2012/0116468 A1 | 5/2012 | Beverland et al. | |

FOREIGN PATENT DOCUMENTS

| | | |
|---|---|---|
| EP | 2168507 | 3/2010 |
| EP | 2491873 | 8/2012 |
| WO | WO 2011117644 | 9/2011 |

OTHER PUBLICATIONS

European Search Report, Appl. No. 13184842.6, dated Nov. 27, 2013.

* cited by examiner

*Primary Examiner* — Anu Ramana
(74) *Attorney, Agent, or Firm* — Barnes & Thornburg LLP

(57) ABSTRACT

A method of reproducing a central axis of a femoral neck prior to resection during an implantation process includes the step of attaching a frame to the acetabulum of a patient, wherein the frame includes first and second movable arms and a lockable swivel bearing. The method further includes the steps of orienting and locking the swivel bearing in position and utilizing the position of the swivel bearing to position acetabular instrumentation to match a planned acetabular implant orientation.

15 Claims, 8 Drawing Sheets

ACETABULAR ORTHOPAEDIC SURGICAL INSTRUMENT AND METHOD OF USING SAME

CROSS-REFERENCE TO RELATED U.S. PATENT APPLICATION

This application claims priority under 35 U.S.C. §119 to U.S. Patent Application No. 61/706,232, entitled "ACETABULAR ORTHOPAEDIC SURGICAL INSTRUMENT AND METHOD OF USING SAME," which was filed on Sep. 27, 2012. The disclosure of such application is incorporated herein by reference.

TECHNICAL FIELD

The present disclosure relates to orthopaedic surgical instruments and more particularly to acetabular orthopaedic surgical instruments.

BACKGROUND

Joint arthroplasty is a well-known surgical procedure by which a diseased and/or damaged natural joint is replaced by a prosthetic joint. For example, in a hip arthroplasty surgical procedure, a prosthetic hip replaces a patient's natural hip. A typical prosthetic hip includes an acetabular orthopaedic prosthesis and/or femoral head orthopaedic prosthesis. A typical acetabular orthopaedic prosthesis includes an acetabular cup, which is secured to the patient's natural acetabulum, and an associated polymer bearing or ring.

To facilitate the replacement of the natural joint with an acetabular orthopaedic prosthesis, orthopaedic surgeons may use a variety of orthopaedic surgical instruments such as, for example, reamers, drill guides, drills, and/or other surgical instruments.

SUMMARY

According to one aspect, a method of reproducing a central axis of a femoral neck prior to resection during an implantation process includes the step of attaching a frame to the acetabulum of a patient, wherein the frame includes first and second movable arms and a lockable swivel bearing. The method further includes the steps of orienting and locking the swivel bearing in position and utilizing the position of the swivel bearing to position acetabular instrumentation to match a planned acetabular implant orientation.

The orienting and locking step may be performed pre-operatively. Alternatively, the orienting and locking step may be performed by a surgeon during an operating procedure.

The frame may include a patient-matched shim.

According to another aspect, a method of reproducing a central axis of a femoral neck prior to resection during an implantation process includes the step of attaching a frame to the acetabulum of a patient. The method further includes the steps of attaching a clamp to a neck of a femur of a patient and connecting the frame and the clamp. The method also includes the steps of moving a neck of the femur until the neck is located in a planned position for the patient and locking the frame and the spring-loaded clamp in the planned position. The planned position is utilized to position acetabular instrumentation to match a planned acetabular implant orientation.

The step of attaching the frame to the acetabulum of a patient may include the steps of attaching the frame to a patient-matched shim and thereafter attaching the shim and frame to the acetabulum of the patient.

The step of attaching the frame may include the steps of adjusting legs of the frame to fit an acetabulum of the patient and securing the frame to the acetabulum of the patient.

The step of attaching the clamp to the neck of the femur of the patient may include the steps of opening spring-loaded arms of the clamp and allowing the spring-loaded arms to close around the neck of the femur of the patient.

The step of connecting the frame and the clamp may include the steps of positioning a first end of a vertical rod through a bore within a swivel bearing within the frame and positioning an L-shaped rod with a first segment thereof through a hole within the clamp and a second segment thereof through a hole within a second end of the vertical rod opposite the first end.

The step of positioning the L-shaped rod may further include the step of aligning features within the vertical rod and the second segment of the L-shaped rod to prevent rotation of the L-shaped rod with respect to the vertical rod.

The locking step may further include the step of tightening a clamp about the swivel bearing to lock the swivel bearing.

The method may further include the steps of removing the L-shaped rod and the vertical rod from the hole within the clamp and the bore through the swivel bearing, respectively, and positioning a rod extending from the acetabular instrumentation within the bore of the swivel bearing to match a planned acetabular implant orientation.

According to yet another aspect, an orthopaedic instrument for facilitating implantation of an acetabular cup component in an acetabulum of a patient includes a frame adapted to be secured to an acetabulum of the patient surrounding a portion of the acetabular cup, wherein the frame includes a swivel bearing. The instrument further includes a clamp adapted to be attached to a neck of a femur of the patient and a translation rod assembly connecting the adjustable frame and the clamp.

The frame may include adjustable legs that are adapted to be adjusted to fit an acetabulum of a patient and are further adapted to be secured to the acetabulum of the patient.

The clamp may include first and second clamp members that are mounted to a handle by springs such that the clamp members are biased toward one another and may be moved away from one another against the bias of a spring to permit the clamp members to engage a femoral neck.

The translation rod assembly may include a vertical rod having a first end extending through a bore in the swivel bearing and an L-shaped rod having a first segment extending through a hole in the clamp and a second segment extending through a hole within a second end of the vertical rod.

The L-shaped rod may include a first feature formed within the vertical rod and a second formed within the second segment of the L-shaped rod. The first and second features cooperate to prevent rotation of the L-shaped rod with respect to the vertical rod.

The swivel bearing may be locked in place to prevent movement of the swivel bearing relative to the frame.

The frame may be attached to a shim that has been matched to a particular patient and the frame and attached shim are implanted within the acetabulum of the patient. The shim and the frame may be formed of a single, integral piece that has been matched to the patient.

The shim may be replaced with another means of setting the frame and swivel bearing orientation relative to the patient.

BRIEF DESCRIPTION OF THE DRAWINGS

The detailed description particularly refers to the following figures, in which.

Other aspects and advantages of the present disclosure will become apparent upon consideration of the following drawings and detailed description, wherein similar structures have similar reference numbers.

DETAILED DESCRIPTION OF THE DRAWINGS

Figure 1:
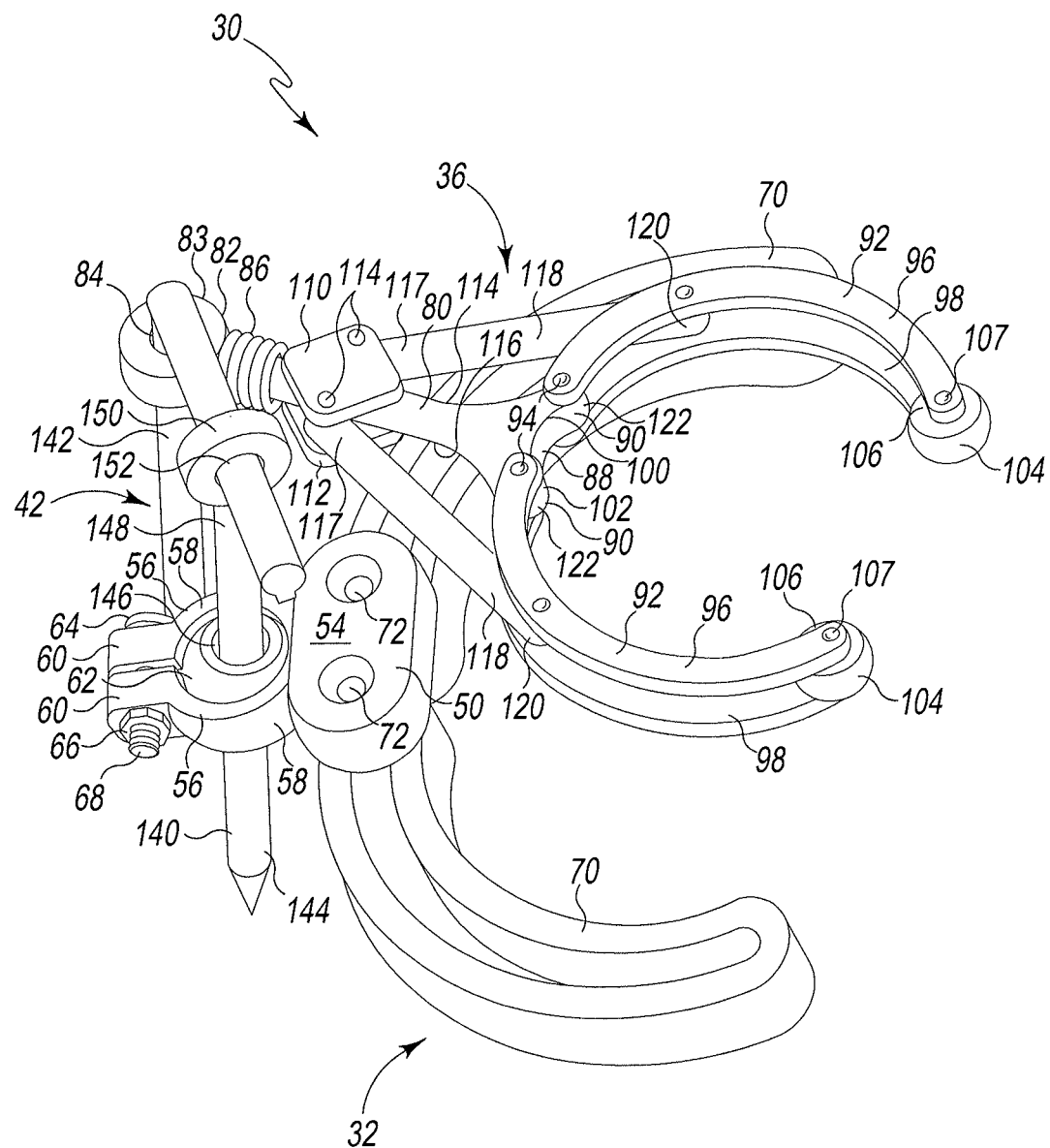
FIG. 1 is a perspective view of a first embodiment of a cup positioning device including a frame for attachment to acetabulum of a hip of a patient, a spring-loaded clamp for attachment to a neck of a femur of the patient, and a translation rod assembly for non-movably positioning the frame and spring-loaded clamp with respect to one another.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-7, a first embodiment of a cup positioning device 30 is depicted. The cup positioning device 30 generally includes a frame 32 that is adapted to be secured to an acetabulum 34 of a hip of a patient, a spring-loaded clamp 36 that is adapted to be attached to a femoral neck 38 of a femur 40 of the patient, and a translation rod assembly 42 that connects the frame 32 and the spring-loaded clamp 36.

The frame 32, the spring-loaded clamp 36, and the translation rod assembly 42 may be made of, for example, medical grade (biocompatible) metals and engineering plastics, including, but not limited to, stainless steel, a titanium alloy, a cobalt chromium alloy, a polyoxymethylene, such as Celcon® or Delrin®, or a polyether ether ketone, or other suitable materials. The frame 32, the spring-loaded clamp 36, and the translation rod assembly 42 may also be made of the same or different materials.

Figure 2:
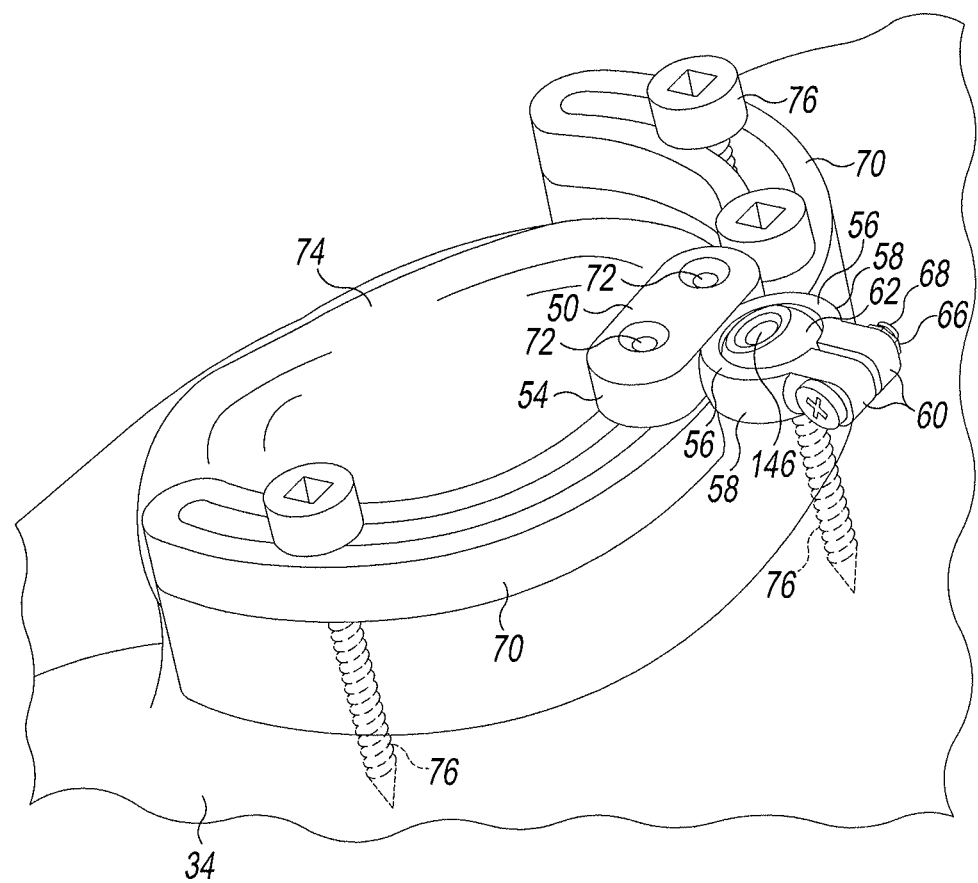
FIG. 2 is a perspective view of the frame of the cup positioning device of FIG. 1 secured to the acetabulum of the hip of the patient.

As best seen in FIGS. 1 and 2, the frame 32 of the cup positioning device 30 includes a central connector 50 having a clamp 52 formed within and connected to and extending from an outer edge 54 of the connector 50. The clamp 52 includes clamp members 56 having curved segments 58 extending from the connector 50 and forming a circular clamp and straight segments 60 extending from the curved segments 58 and parallel to one another. A swivel bearing 62 is disposed within the circular clamp adjacent the curved segments 58 and a fastener 64 extends through the straight segments 60. A nut 66 is attached to a free end 68 of the fastener 64. Tightening of the nut 66 on the fastener 64 causes movement of the straight segments 60 toward one another, thereby moving the curved segments 58 toward each other and causing the curved segments 58 to clamp and prevent movement of the swivel bearing 62, as will be discussed in greater detail below.

While the fastener 64 and the nut 66 are shown as tightening and locking the clamp 52, other suitable methods for tightening and locking the clamp 52 may be utilized. Still further, any clamp or other suitable structure that would allow the swivel bearing 62 to be rotated and locked, as desired by a user, may be utilized.

Still referring to FIGS. 1 and 2, the frame 32 further includes arms 70 extending from and attached to the connector 50 by pins 72. The pins 72 extend through the connector and the arms 70 to form a point of rotation such that the arms 70 may be rotated with respect to the connector 50. Each of the arms 70 is secured to the acetabulum 34 of the patient surrounding an acetabular anatomy 74 by two or more anchors 76, as seen in FIG. 2. The anchors 76 may be in the form of screws, bolts, or any other structure suitable for securing the arms 70 to the acetabulum 34. The anchors 76 are positioned to prevent movement of the arms 70 and connector 50 with respect to one another.

Figure 3:
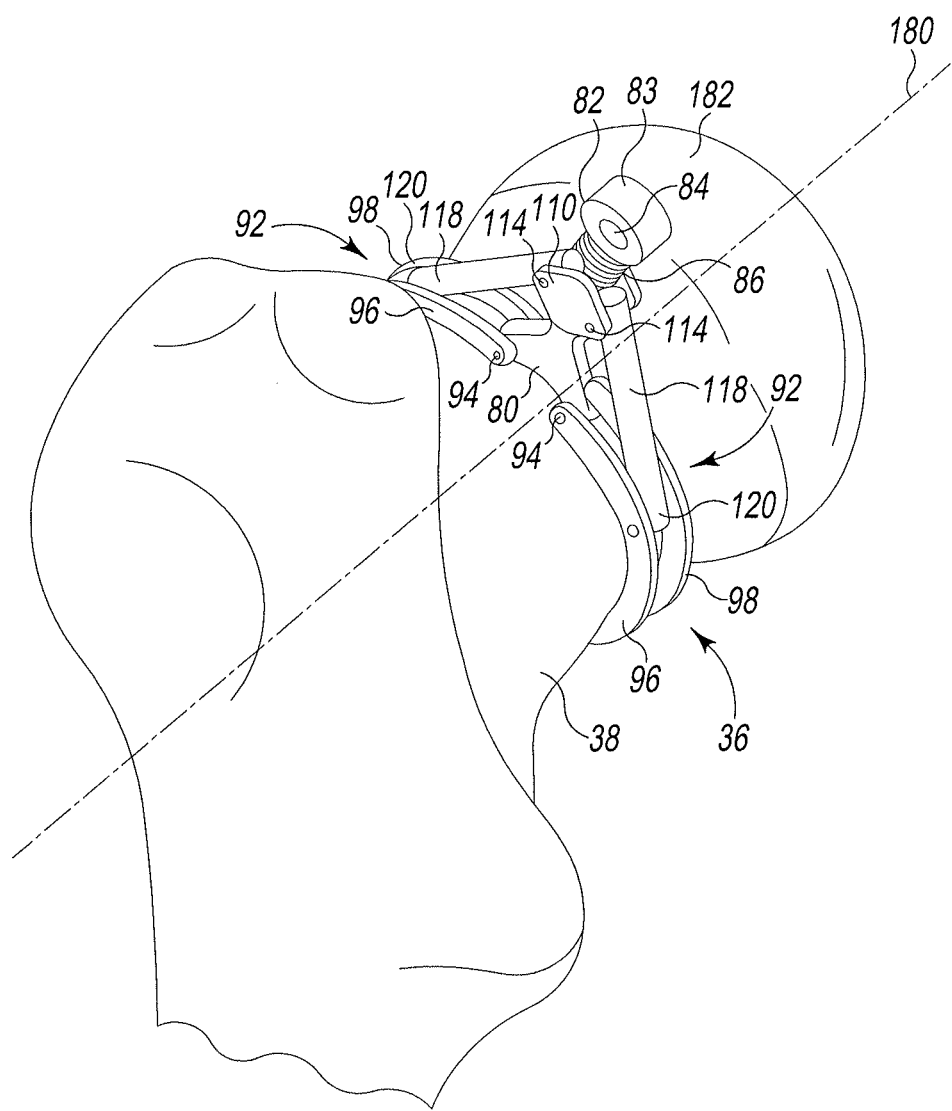
FIG. 3 is a perspective view of the spring-loaded clamp of the cup positioning device of FIG. 1 attached to the neck of the femur of the patient.

The spring-loaded clamp 36, as best seen in FIGS. 1 and 3, includes a handle 80 having a support end 82 having an enlarged head 83 with a hole 84 therethrough. The support end 82 has a width larger than a width of the handle 80 to retain a spring 86 on the handle 80 adjacent the support end 82. A clamp end 88 of the handle 80 further includes spherical projections 90 that extend outwardly from sides of the handle 80. Clamp members 92 are attached to the spherical projections 90 by pins 94 or other suitable structures that allow pivoting. While the projections 90 are shown and disclosed as being spherical, other suitable shapes that limit damages to bone may be utilized.

Each clamp member 92 includes upper and lower curved arms 96, 98 that are attached to upper and lower surfaces 100, 102 of the spherical projections 90, respectively, by the pins 94. Knobs 104 are disposed between the upper and lower curved arms 96, 98 at ends 106 of the clamp members 92. The knobs 104 may be attached by pins 107 or any other suitable structure that allows rotation of the knobs 104. Optionally, the knobs 104 may be stationary. The knobs 104 may be made of a material and/or formed in a shape that prevents damage to bone. For example, the knobs 104 may be rounded or oval-shaped and/or the knobs 104 may be made of, for example, rubber or plastic. While the knobs 104 are shown as being partially spherical in shape, other suitable shapes may alternatively be utilized.

Still referring to FIGS. 1 and 2, the spring-loaded clamp 36 further includes upper and lower plates 110, 112 disposed against upper and lower surfaces 114, 116 of the handle 80. The plates 110, 112 are connected by pins 114 or another suitable structure to first ends 117 of links 118, wherein second ends 120 of the links 118 are connected to the upper and lower curved arms 96, 98 of the clamp members 92.

The plates 110, 112 are positioned for movement along the upper and lower surfaces 114, 116 of the handle 80. In particular, the spring 86 is disposed over the handle 80 between the support end 82 of the handle 80 and the plates 110, 112. When unactuated, the spring 86 is biased against the plates 110, 112, thereby pushing the plates toward the clamp end 88 of the handle 80, causing the links 118 to close the clamp members 92. As will be discussed in greater detail below, when the knobs 104 are pressed against a structure for clamping, for example, the neck 38 of the femur 40, outward pressure on the knobs 104 causes the clamp members 92 to move outwardly. Outward movement of the clamp members 92 causes inward movement and straightening of the links 118, which causes movement of the plates 110, 112 toward the support end 82 of the handle 80 against the bias of the spring 86. Once the knobs 104 have passed the femoral neck 38, the clamp members 92 return to their original, biased position with the clamp members 92 attached to the femoral neck 38. In this position, the knobs 104 and outer surfaces 122 of the spherical projections 90 are in contact with the femoral neck 38.

Figure 4:
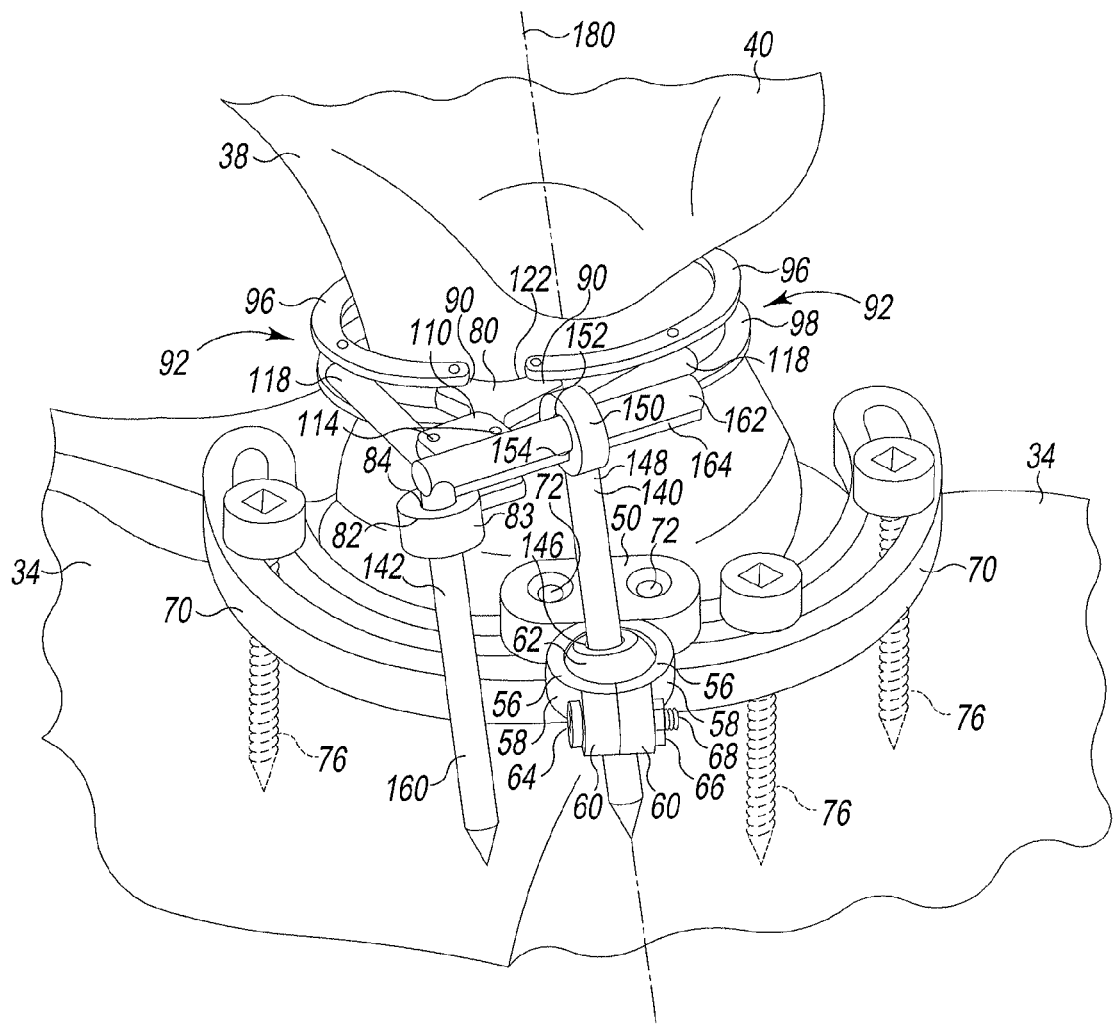
FIG. 4 is a perspective view of the frame secured to the acetabulum of the hip of the patient, the spring-loaded clamp attached to the neck of the femur of the patient, the translation rod assembly attached to and connecting the frame and the spring-loaded clamp, wherein the femur of the patient has been rotated until a planned position for articulation of a head of the femur within the acetabular cup is reached and a swivel bearing within the frame has been locked to secure the cup positioning device in that planned position.
Figure 5:
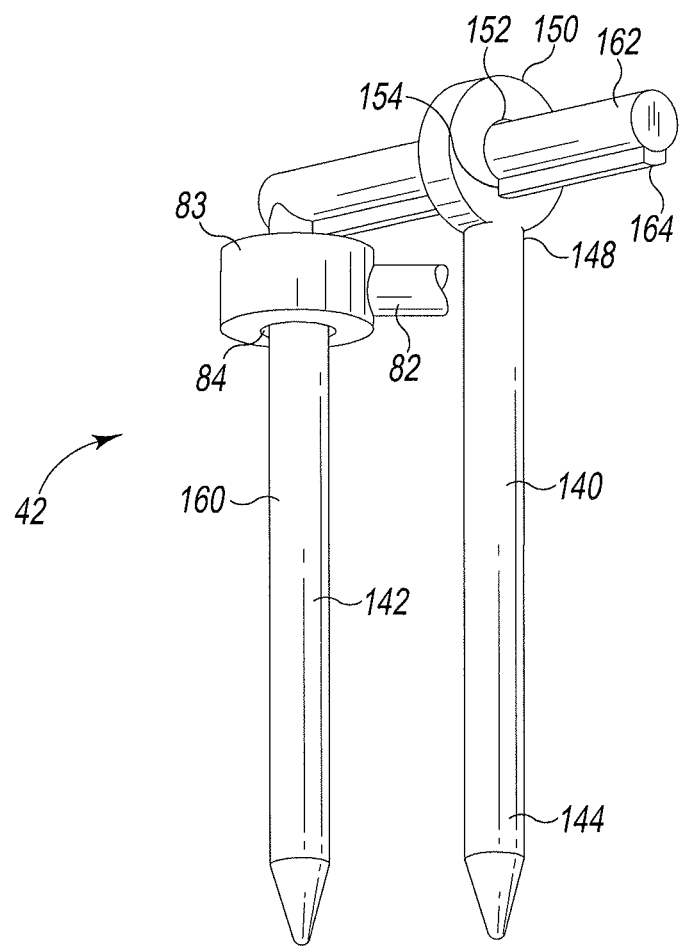
FIG. 5 is a perspective view of the translation rod assembly showing a lock and key in rods of the translation rod assembly to prevent relative rotation.

Referring to FIGS. 1, 4, and 5, the translation rod assembly 42 includes a vertical rod 140 and an L-shaped rod 142. The vertical rod 140 is generally cylindrical and includes a lower end 144 that extends through a bore 146 that extends through the swivel bearing 62. An upper end 148 of the vertical rod 140 includes an enlarged head 150 with a hole 152 therethrough. As can best be seen in FIG. 5, the hole 152 is generally circular with a square-shaped cutout 154 at a lower edge of the hole 152, as will be discussed in greater detail below.

The L-shaped rod 142 includes a vertical segment 160 that extends through the hole 84 in the support end 82 of the handle 80 of the spring-loaded clamp 36. The L-shaped rod 142 also includes a horizontal segment 162 that is connected to and extends at an angle of about 90 degrees from the vertical segment 160. The vertical and horizontal segments 160, 162 are generally cylindrical, although the horizontal segment 162 includes a square-shaped projection 164 extending from a lower surface 166 thereof. As best seen in FIG. 5, the horizontal segment 162 extends through the hole 152 in the enlarged head 150 of the vertical rod 140 with the square-shaped projection 164 disposed within the square-shaped cutout 154 of the hole 152 to prevent rotation of the horizontal segment 162 within the hole 152. The square-shaped cutout 154 and projection 164 also provide a lock and key mechanism whereby the vertical rod 140 and the L-shaped rod 142 may only be attached in one manner. Although a square-shaped cutout 154 and projection 164 are shown and described, other complementary or non-complementary shapes, for example, semi-circular, triangular, hexagonal, rectangular, and the like, may be utilized to prevent rotational movement of the horizontal segment 162 within the hole 152. In addition, while the square-shaped cutout 154 and projection 164 are shown as being on lower surfaces of the hole 152 and the horizontal segment 162, respectively, the cutout 154 and the projection 164 may be located on other surfaces that allow the projection 164 to be aligned within the cutout 154. Still further, any other mechanisms for preventing rotation may be utilized.

Ends of the vertical rod 140 and the vertical segment 160 may be tapered to facilitate insertion through the hole 84 and the bore 146, respectively. While the vertical rod 140 and the vertical and horizontal segments 160, 162 of the L-shaped rod 142 are generally described as cylindrical, other suitable shapes may be utilized.

Figure 6:
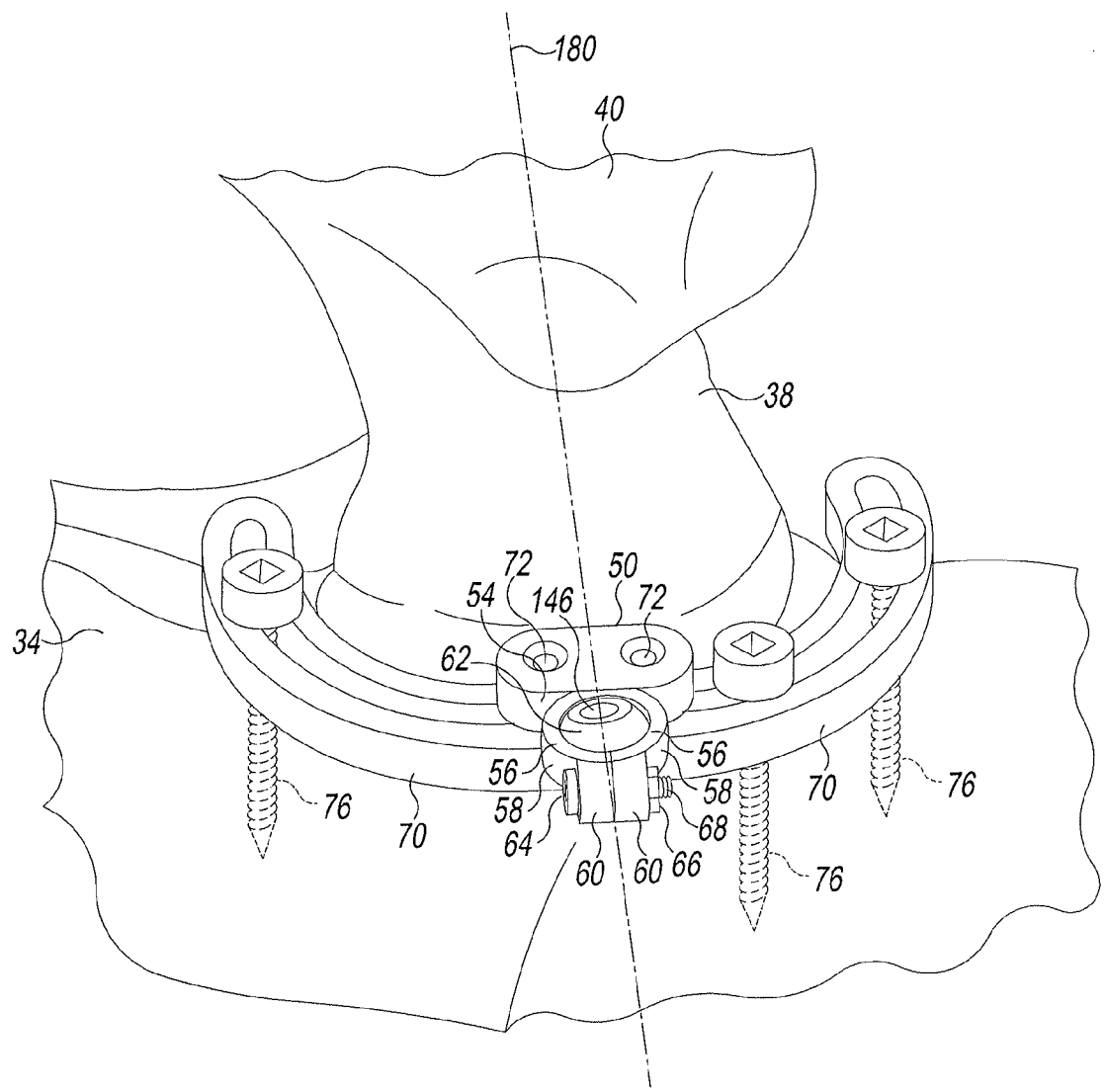
FIG. 6 is a perspective view of the frame with the swivel bearing locked in position and the translation rod assembly and spring-loaded clamp removed therefrom.

An exemplary method of using the cup positioning device 30 of FIGS. 1-7 will now be described in detail with respect to FIGS. 2-4, 6, and 7. The cup positioning device provides a method for reproducing a central axis 180 of the femur 40 (as shown in FIGS. 3, 4, and 6) prior to re-section so the central axis 180 may be utilized to properly position an acetabular cup implant component. It will be appreciated that details of the surgical procedure may vary, for instance, according to the preferences of the surgeon. For example, a surgeon may perform the steps in a different order and/or may add or remove particular steps.

Each patient has different anatomy, but there is a relationship (e.g., a neck angle) between an anatomical axis of the femoral neck 38 and an anatomical plane of the acetabulum 34. The surgeon selects a proximal femoral implant with a given neck angle, wherein there exists a delta between the anatomical axis of the femoral neck 38 and an axis of a neck of the femoral implant. The neck angle has a relationship to the placement and orientation of the acetabular cup implant component that ensures a range of motion without impingement.

Referring to FIG. 2, the frame 32 of the cup positioning device 30 is positioned on the acetabulum 34 around a perimeter of the acetabular anatomy 74. The arms 70 of the frame 32 may be pivoted about the point of rotation formed between the arms 70 and the connector 50 at the pins 72 to account for different sized acetabular cups 74. Once the arms 70 are positioned about the perimeter of the acetabular anatomy 74, the arms 70 are secured to the acetabulum 34 by the anchors 76.

As seen in FIG. 3, the spring-loaded clamp 36 is attached to the neck 38 of the femur 40. As discussed above, the knobs 104 are pushed against the femoral neck 38, which causes outward movement of the clamp members 92. Once the knobs 104 have passed the femoral neck 38, the clamp members 92 return to their original, biased position with the clamp members 92 attached to the femoral neck 38. In this position, the knobs 104 and outer surfaces 122 of the spherical projections 90 are in contact with the femoral neck 38 to prevent movement of the spring-loaded clamp 36. While attachment of the frame 32 to the acetabulum 34 is discussed as preceding attachment of the spring-loaded clamp 36 to the femoral neck 38, these steps may be reversed.

After the frame 32 has been attached to the acetabulum 34 and the spring-loaded clamp 36 has been attached to the femoral neck 38, the translation rod assembly 42 is connected to the frame 32 and the spring-loaded clamp 36. In particular, the spring-loaded clamp 36 is rotated about the femoral neck 38 until the enlarged head 83 of the handle 80 is spaced from the swivel bearing 62 of the frame 32, as best seen in FIG. 4. The horizontal segment 162 of the L-shaped rod 162 is inserted through the hole 152 in the enlarged head 150 of the vertical rod 140 with the square-shaped cutout 154 and the square-shaped projection 164 aligned to prevent rotation of the horizontal segment 162 within the hole 152. The translation rod assembly 42 is thereafter attached to the frame 32 and the spring-loaded clamp 36 by inserting the vertical segment 160 of the L-shaped rod 142 through the hole 84 in the enlarged head 83 of the handle 80 of the spring-loaded clamp 36 until the horizontal segment 162 is in contact with the enlarged head 83. Simultaneously, the vertical rod 140 is inserted through the bore 146 in the swivel bearing 62 until the horizontal segment 162 is in contact with the enlarged head 83. Optionally, the vertical rod 140 and the L-shaped rod 142 may be separately attached to the frame 32 and the spring-loaded clamp 36.

Once the translation rod assembly 42 is properly attached to the frame 32 and the spring-loaded clamp 36, the femur 40 of the patient is articulated by the calculated delta so that the anatomic neck axis is parallel to the cup placement axis, thereby reaching the planned position for articulation of a head 182 of the femur 40 within the acetabular anatomy 74. The femur 40 is thereafter locked in place, as seen in FIG. 4, for example, by tightening the nut 66 on the fastener 64, which causes movement of the straight segments 60 of the clamp 52 toward one another, thereby moving the curved segments 58 toward each other and causing the curved segments 58 to clamp and prevent movement of the swivel bearing 62. In this position, the vertical rod 140 and the vertical segment 160 of the L-shaped rod 142 are parallel to the central axis 180 of the femoral neck 38, as will be described in greater detail below.

Referring to FIG. 6, the translation rod assembly 42 is removed from the frame 32 and the spring-loaded clamp 36 and the spring-loaded clamp 36 is removed from the femoral neck 38. The femoral head 182 is either re-sected while positiond within the acetabular anatomy 74 or removed from the acetabular anatomy 74 and thereafter re-sected. Regardless, once the femoral head 182 has been re-sected and removed from the acetabular anatomy 74, the acetabular instrumentation 200 is attached to the frame 32 to properly prepare the acetabular anatomy 74 for positioning of the acetabular cup implant component. While any acetabular instrumentation 200 may be used, the acetabular instrumentation 200 is shown as a reamer generally including a shaft 204 and a cup reamer 206 attached to the shaft 204 for reaming the acetabular anatomy 74.

Figure 7:
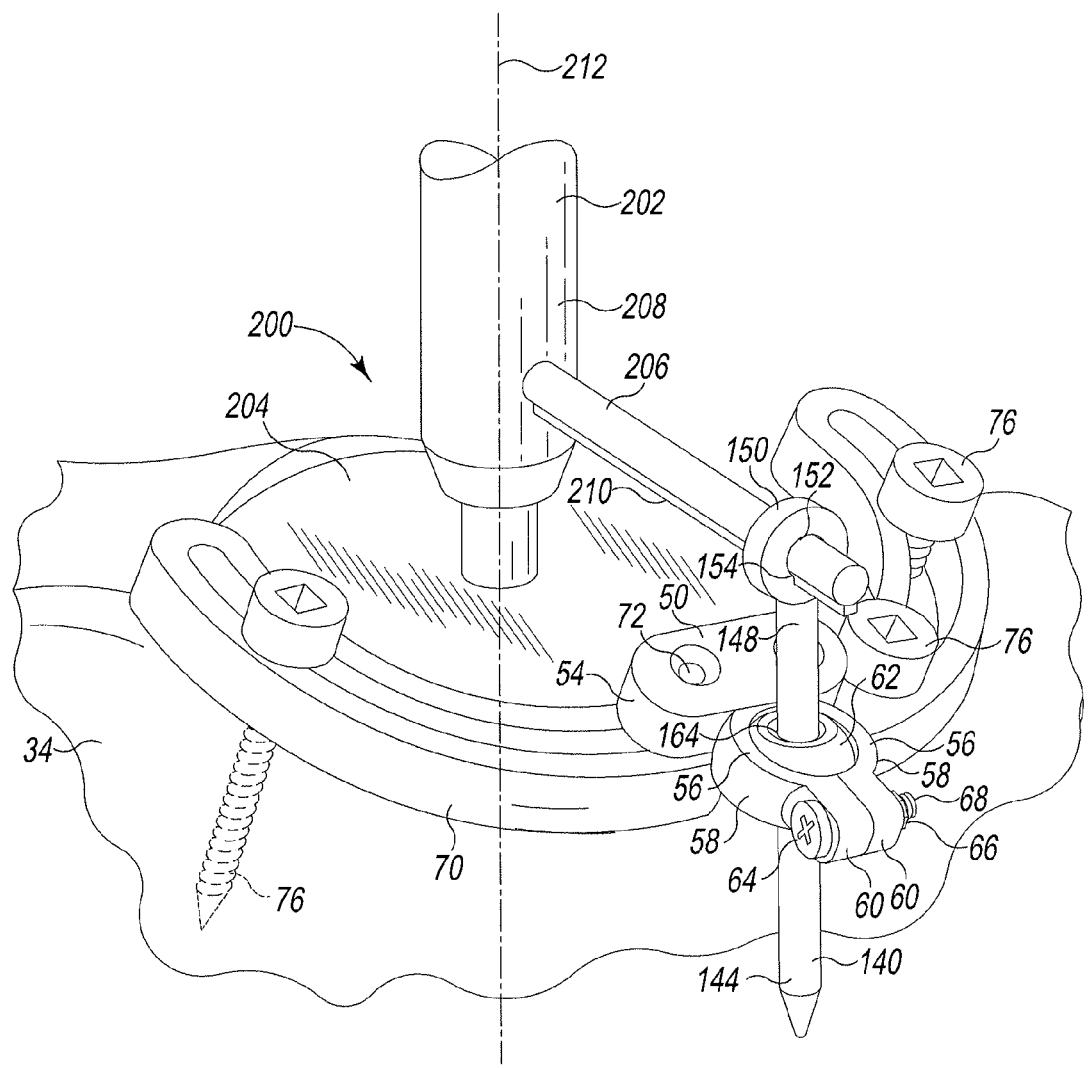
FIG. 7 is a perspective view similar to FIG. 6 with a acetabular cup reamer connected to the swivel bearing by a translation rod assembly.

A rod 206, as seen in FIG. 7, extends outwardly from an outer surface 208 of the shaft 204 at an angle of about 90 degrees. The rod 206 is generally cylindrical and includes a square-shaped projection 210. The rod 206 is inserted through the hole 152 of the vertical rod 140 with square-shaped projection 210 aligned with and retained within the square-shaped cutout 154 of the hole 152. Simultaneously, the cup reamer 206 is positioned within the acetabular anatomy 74 and the vertical rod 140 is inserted through the bore 146 of the swivel bearing 62. In this position, the planned position for articulation of the femoral head 182 within the acetabular anatomy 74 is replicated. In particular, the swivel bearing 62 allows the vertical rod 140 to position the acetabular instrumentation 200 with a central axis 212 positioned parallel to the central axis 180 of the femoral neck 38. Optionally, the vertical rod 140 may position the acetabular instrumentation 200 (and other tools) in a position that is not parallel to the central axis 180. In this manner, the acetabular instrumentation 200 is precisely oriented to match a planned acetabular implant orientation.

Figure 8:
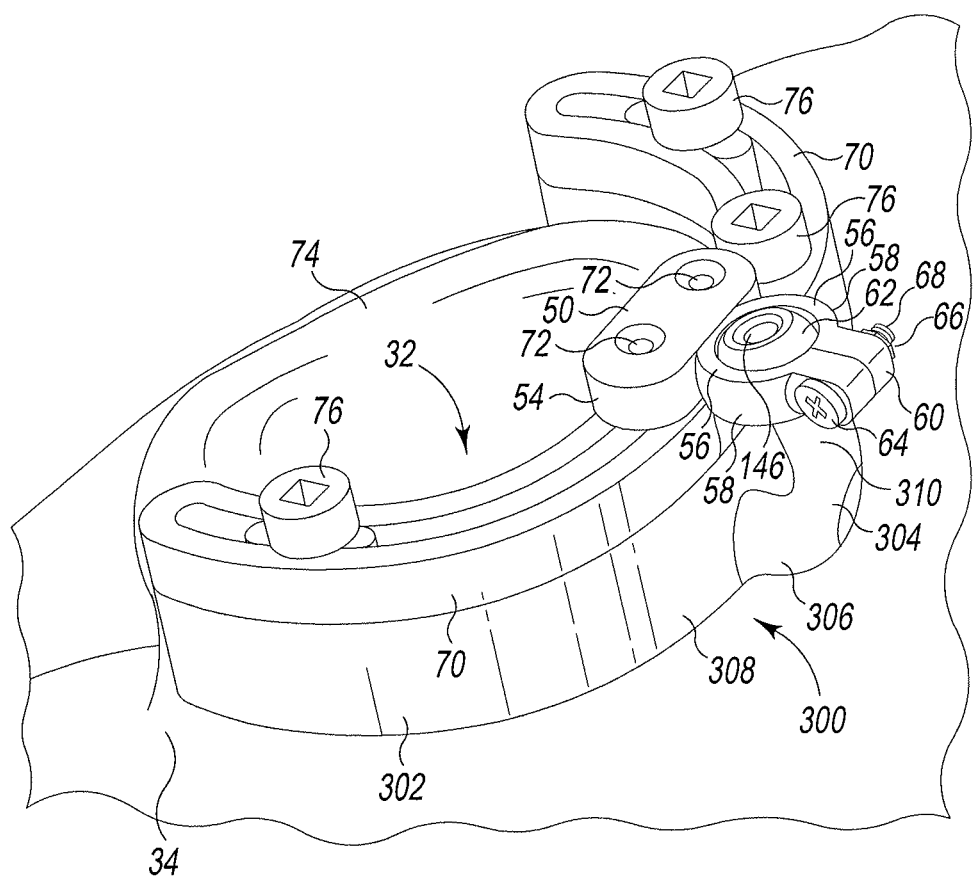
FIG. 8 is a perspective view of a second embodiment of a cup positioning device including a patient-matched shim attached to an acetabulum of a hip of a patient and a frame secured to the patient-matched shim and the acetabulum, wherein a swivel bearing within the frame is pre-positioned and locked in position.

A second embodiment of a cup positioning device 300 is depicted in FIG. 8. The cup positioning device 300 includes a patient-matched shim 302, the shape and size of which are matched to a patient based on pre-operative imaging. More specifically, the shim 302 is designed to fit around a perimeter of the acetabulum 34. Features of the shim 302 on a face 304 opposite the bone surface are designed to locate the frame 32 and the orientation of the bore 146 of the swivel bearing 62.

The method of using the cup positioning device 300 of FIG. 8 includes the step of adjusting the arms 70 of the frame 32 by pivoting the arms 70 about the pins 72 such that the frame 32 is sized to fit the shim 302. The frame 32 is thereafter attached to or otherwise held together with the shim 302 and the combination of the frame 32 and the shim 302 is secured to the acetabulum 34 by the anchors 76, which extend through the frame 32 and the shim 302 and into the acetabulum 34. The frame 32 and the shim 302 may be attached during manufacture and/or design of the patient-matched cup positioning device 300. Optionally, the frame 32 and the shim 302 may be attached prior to introducing them to a wound site (but after manufacture and design) or after the shim 302 is initially placed on the bone within the wound. Regardless of the method used, once the frame 32 and the shim 302 are adjacent the bone, anchors 76 are inserted through the frame 32 and the shim 302 into the bone.

The shim 302 orients the frame 32 and the bore 146 of the swivel bearing 62 relative to the pre-operative plan and then the plan is translated to the anatomy when the shim 302 is seated on the perimeter of the acetabulum 34. In this manner, the spring-loaded claim 36 and translation rod assembly 42 of the embodiment of FIGS. 1-7 are not necessary.

Once the frame 32 and the shim 302 are secured to the acetabulum 34, the rod 202 of the acetabular instrumentation 200 is inserted through the hole 152 within the vertical rod 140 as disclosed in detail with respect to FIG. 7 and the acetabular instrumentation 200, for example a reamer, is used to ream the acetabular anatomy 74 for implantation of an acetabular cup implant component as described in detail above. A cup impactor or other surgical tools may additionally be guided by the rods 140, 202.

While the shim 302 and the frame 32 are shown as separate components, the shim 302 and the frame 32 may be integral. In this manner, the shim 302 and the frame 32 may be matched to a particular patient.

As will become apparent from reading the present specification, any of the features of any of the embodiments disclosed herein may be incorporated within any of the other embodiments without departing from the scope of the present disclosure.

Further, although directional terminology, such as front, back, top, bottom, upper, lower, etc. may be used throughout the present specification, it should be understood that such terms are not limiting and are only utilized herein to convey the orientation of different elements with respect to one another.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic instrument assembly for facilitating implantation of an acetabular cup component in an acetabulum of a patient, the instrument comprising:
   a frame adapted to be secured to an acetabulum of the patient surrounding a portion of the acetabular cup, wherein the frame includes a swivel bearing;
   a clamp adapted to be attached to a neck of a femur of the patient; and
   a translation rod assembly connecting the frame and the clamp,
   wherein the frame includes adjustable legs that are adapted to be adjusted to fit an acetabulum of a patient and are further adapted to be secured to the acetabulum of the patient.

2. The orthopaedic instrument assembly of claim 1, wherein the clamp includes first and second clamp members mounted to a handle by a spring such that the clamp members are biased toward one another and may be moved away from one another against the bias of a spring to permit the clamp members to engage a femoral neck.

3. The orthopaedic instrument assembly of claim 1, wherein the translation rod assembly includes:
   a vertical rod having a first end extending through a bore in the swivel bearing; and
   an L-shaped rod having a first segment extending through a hole in the clamp and a second segment extending through a hole within a second end of the vertical rod.

4. The orthopaedic instrument assembly of claim 3, wherein the L-shaped rod includes:
   a first feature formed within the vertical rod; and
   a second feature formed within the second segment of the L-shaped rod;
   wherein the first and second features cooperate to prevent rotation of the L-shaped rod with respect to the vertical rod.

5. The orthopaedic instrument assembly of claim 4, wherein the swivel bearing is locked in place to prevent movement of the swivel bearing relative to the frame.

6. An orthopaedic instrument assembly for facilitating implantation of an acetabular cup component in an acetabulum of a patient, the instrument comprising:
   a frame adapted to be secured to an acetabulum of the patient surrounding a portion of the acetabular cup, wherein the frame includes a swivel bearing;
   a clamp adapted to be attached to a neck of a femur of the patient; and
   a translation rod assembly connecting the frame and the clamp,
   wherein the clamp includes first and second clamp members mounted to a handle by a spring such that the clamp members are biased toward one another and may be moved away from one another against the bias of a spring to permit the clamp members to engage a femoral neck.

7. The orthopaedic instrument assembly of claim 6, wherein the frame includes adjustable legs adapted to be secured to the acetabulum of the patient.

8. The orthopaedic instrument assembly of claim 7, wherein the translation rod assembly includes:
   a vertical rod having a first end extending through a bore in the swivel bearing; and
   an L-shaped rod having a first segment extending through a hole in the clamp and a second segment extending through a hole within a second end of the vertical rod.

9. The orthopaedic instrument assembly of claim 8, wherein the L-shaped rod includes:
   a first feature formed within the vertical rod; and
   a second feature formed within the second segment of the L-shaped rod;
   wherein the first and second features cooperate to prevent rotation of the L-shaped rod with respect to the vertical rod.

10. The orthopaedic instrument assembly of claim 9, wherein the swivel bearing is locked in place to prevent movement of the swivel bearing relative to the frame.

11. An orthopaedic instrument assembly for facilitating implantation of an acetabular cup component in an acetabulum of a patient, the instrument comprising:
    a frame adapted to be secured to an acetabulum of the patient surrounding a portion of the acetabular cup, wherein the frame includes a swivel bearing;
    a clamp adapted to be attached to a neck of a femur of the patient; and
    a translation rod assembly connecting the frame and the clamp, wherein the translation rod assembly includes:
    a vertical rod having a first end extending through a bore in the swivel bearing; and
    an L-shaped rod having a first segment extending through a hole in the clamp and a second segment extending through a hole within a second end of the vertical rod.

12. The orthopaedic instrument assembly of claim 11, wherein the L-shaped rod includes:
    a first feature formed within the vertical rod; and
    a second feature formed within the second segment of the L-shaped rod;
    wherein the first and second features cooperate to prevent rotation of the L-shaped rod with respect to the vertical rod.

13. The orthopaedic instrument assembly of claim 11, wherein the swivel bearing is locked in place to prevent movement of the swivel bearing relative to the frame.

14. The orthopaedic instrument assembly of claim 11, wherein the frame includes adjustable legs adapted to be secured to the acetabulum of the patient.

15. The orthopaedic instrument assembly of claim 11, wherein the clamp includes first and second clamp members mounted to a handle by a spring such that the clamp members are biased toward one another and may be moved away from one another against the bias of a spring to permit the clamp members to engage a femoral neck.

* * * * *